(12) United States Patent
Moutou et al.

(10) Patent No.: US 9,012,667 B2
(45) Date of Patent: Apr. 21, 2015

(54) PROCESS FOR INTRODUCING A DOUBLE BOND INTO POSITION 15, 16 OF A STEROID

(75) Inventors: Jean-Luc Moutou, Cagnes sur Mer (FR); Florent Mouton, Saint-Laurent du Var (FR); Gilles Pellegrino, Menton (FR); Jean-Marc Dillenschneider, Nice (FR); Jean Lafay, Nice (FR)

(73) Assignee: Laboratoire Theramex, Monaco (MC)

( * ) Notice: Subject to any disclaimer, the term of this patent is extended or adjusted under 35 U.S.C. 154(b) by 0 days.

(21) Appl. No.: 13/578,062

(22) PCT Filed: Feb. 8, 2011

(86) PCT No.: PCT/EP2011/051783
§ 371 (c)(1),
(2), (4) Date: Feb. 14, 2013

(87) PCT Pub. No.: WO2011/098439
PCT Pub. Date: Aug. 18, 2011

(65) Prior Publication Data
US 2013/0137885 A1    May 30, 2013

(30) Foreign Application Priority Data
Feb. 9, 2010   (EP) .................................... 10305133

(51) Int. Cl.
*C07J 1/00*    (2006.01)
(52) U.S. Cl.
CPC . *C07J 1/00* (2013.01); *C07J 1/0059* (2013.01)
(58) Field of Classification Search
USPC .......................................... 552/502, 642, 648
See application file for complete search history.

(56) References Cited

U.S. PATENT DOCUMENTS

| 3,214,448 | A | * | 10/1965 | Holmlund et al. | 552/618 |
| 4,036,695 | A | * | 7/1977 | Petzoldt et al. | 552/510 |
| 4,081,537 | A | | 3/1978 | Hofmeister et al. | |
| 4,371,529 | A | | 2/1983 | Hofmeister et al. | |
| 4,464,365 | A | | 8/1984 | Hofmeister et al. | |
| 4,719,054 | A | | 1/1988 | Hofmeister et al. | |
| 5,382,434 | A | * | 1/1995 | de Haan et al. | 424/465 |
| 5,976,570 | A | * | 11/1999 | Greaves et al. | 424/470 |

FOREIGN PATENT DOCUMENTS

| DE | 2546062 | 4/1977 |
| EP | 0051762 | 5/1982 |
| EP | 0092174 | 10/1983 |
| EP | 0201452 | 11/1986 |
| EP | 0700926 | 3/1996 |
| EP | 1586579 | 10/2005 |
| FR | 2326927 | 5/1977 |

OTHER PUBLICATIONS

Norris, J.F. "Experimental Organic Chemistry" McGraw-Hill Book Company. New York. 1924. Ch 1, pp. 1-3.*
Hofmeister et al.: "Synthesis of Gestoden"; Arzneimittel-Forschung, Drug. Reg. 36 (1), No. 5, pp. 781-783, 1986—together with English summery and Abstract by Europe PubMed Central.
Hofmeister et al.; "Syntheses of Gesodene (Synthesen von Gestoden)", Arzneimittel-Forschung May 1986 LNKD-PUBMED: 3730011, vol. 36, No. 5, pp. 781-783.

* cited by examiner

*Primary Examiner* — Sabiha N Qazi
(74) *Attorney, Agent, or Firm* — Hamre, Schumann, Mueller & Larson, P.C.

(57) ABSTRACT

The invention relates to a process for the preparation of a compound of formula (I):

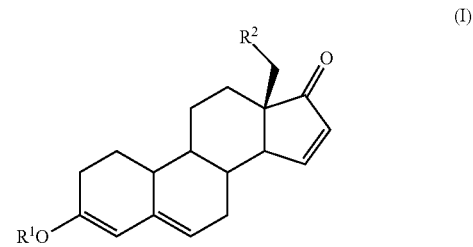

wherein $R^1$ and $R^2$ are as defined in the description, by reaction of a compound of formula (II)

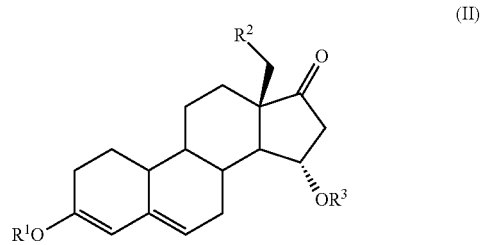

with a base.
Compound (I) is an intermediate useful in the preparation of gestodene.

13 Claims, 5 Drawing Sheets

Impurity A

Impurity B

Impurity C

Impurity D

Impurity E

Impurity F

FIG.2

Impurity G

Impurity H

Impurity I

Impurity J

Impurity K

Impurity L

FIG.2 (continued)

PROCESS FOR INTRODUCING A DOUBLE BOND INTO POSITION 15, 16 OF A STEROID

FIELD OF THE INVENTION

The present invention relates to a process for the preparation of intermediates which are useful for the synthesis of gestodene. The invention also relates to a process for the preparation of gestodene. The invention further relates to a process for introducing a double bond into position 15,16 of a steroid.

BACKGROUND OF THE INVENTION

Gestodene (17-alpha-ethynyl-17-beta-hydroxy-18-methyl-estra-4,15-dien-3-one) is a progestin mainly used as an oral contraceptive, in combination with an oestrogen. This molecule, which was described for the first time in German patent application DE2546062, is a third generation progestin with low androgenic activity.

Gestodene is usually prepared from a hydroxylated intermediate (15-hydroxy-18-methyl-estr-4-en-3,17-dione) which is converted into the desired product by means of a process which comprises the protection of the ketone in position 3 as a ketal, the esterification of the hydroxyl in position 15 and the ethynylation of the ketone in position 17 (see e.g. FR-A-2326927 and EP-A-700926). An alternative route, described by Hofmeister in Arzneim. Forsch. 1986, 36(1), 781-783 or in EP-A-201452, also starts from 15-hydroxy-18-methyl-estr-4-en-3,17-dione, but comprises the protection of the ketone in position 3 as a methyl enol ether, the acylation of the hydroxyl in position 15, and then the introduction of the ethynyl in position 17 (see preparation 2 and example 1b). EP-A-201452 also describes another alternative route comprising the conversion of 15-hydroxy-18-methyl-estr-4-en-3, 17-dione into 18-methyl-estra-4,15-dien-3,17-dione, the protection of the ketone in position 3 as a methyl enol ether and then the introduction of the ethynyl in position 17 (see preparation 1 and example 1a). Another process, described in EP-A-1586579, comprises the protection of the ketone in position 3 as a ketal, and the introduction of a phenyl sulphide or phenyl sulfoxide in position 16 which affords the double bond in position 15,16 by elimination.

The crucial step for the synthesis of gestodene is precisely the timely introduction of the double bond at this specific 15,16 position. Introduction of the double bond with concomitant ethynylation in position 17 (as described e.g. in example 1b-d of EP-A-201452) is prone to competition between the elimination of the group in position 15 and the ethynylation in position 17. Introduction at an earlier stage of the synthesis (as described e.g. in preparation 1 of EP-A-201452) may result in impurities being obtained. In each case, this may be detrimental to the overall synthesis yield.

It is therefore an object of the present invention to provide a process for the synthesis of gestodene which is devoid of the drawbacks of the above-mentioned processes. It is in particular an object of the present invention to provide a process which is simple to implement and which makes it possible to obtain gestodene in high purity and yield.

DESCRIPTION OF THE INVENTION

The inventors have surprisingly found that $\Delta^{15}$ steroids can be efficiently synthesized when the double bond in position 15,16 is introduced under mild conditions at an early stage of the process for synthesizing the said steroid. This is achieved by synthesizing in the first place a key steroid intermediate starting from a precursor bearing a specific substituent in position 15.

Accordingly, a first aspect of the present invention relates to a process for the preparation of a compound of formula (I):

wherein $R^1$ is a $(C_1\text{-}C_4)$alkyl, preferably methyl or ethyl, and $R^2$ is H or methyl, which comprises the reaction of a compound of formula (II) with a base:

wherein:
$R^1$ and $R^2$ are as defined above;
$R^3$ is $-COR^4$; and
$R^4$ is a $(C_1\text{-}C_6)$alkyl; a phenyl optionally substituted with 1 to 3 $(C_1\text{-}C_4)$alkyl; or a benzyl in which the phenyl is optionally substituted with 1 to 3 $(C_1\text{-}C_4)$alkyl.

A suitable base for carrying out the reaction of compound (II) may be selected from a metal carbonate; a metal bicarbonate; a metal hydroxide; a metal hydride; a metal acetate; ammonia; and an amine of formula $NR^5R^6R^7$ where
$R^5$, $R^6$ and $R^7$ each independently represent H; a $(C_1\text{-}C_6)$ alkyl optionally substituted by a hydroxyl; or a $(C_3\text{-}C_6)$cycloalkyl (and at least one of $R^5$, $R^6$ and $R^7$ is not H);

or $R^5$ is H and $R^6$ and $R^7$ form, together with the nitrogen atom to which they are bonded, a 5- to 7-membered saturated heterocycle which may optionally contain another heteroatom selected from O and N.

In the description and appended claims, the term "alkyl" refers to a straight-chain or branched-chain saturated aliphatic hydrocarbon radical containing the specified number of carbon atoms. Examples of alkyl radicals include methyl, ethyl, n-propyl, isopropyl, n-butyl, isobutyl, sec-butyl, tert-butyl, pentyl, isopentyl or hexyl.

The term "cycloalkyl" refers to a saturated monocyclic hydrocarbon radical containing the specified number of carbon atoms. Examples of cycloalkyl radicals include cyclopropyl, cyclobutyl, cyclopentyl, cyclohexyl.

The term "halogen" refers to an atom of chlorine, bromine, fluorine or iodine.

Examples of 5- to 7-membered saturated heterocycles include pyrrolidine, piperidine, piperazine, and morpholine.

In one embodiment, the base is a metal carbonate. Suitable metals include alkali metals (such as sodium, potassium, lithium, caesium), alkaline earth metals (such as magnesium, calcium), copper, aluminium, zinc and iron. Alkali metal carbonates are preferred.

In another embodiment, the base is a metal bicarbonate. Suitable metals include alkali metals (such as sodium, potassium).

In another embodiment, the base is a metal hydroxide. Suitable metals include alkali metals (such as sodium, potassium, lithium, caesium), alkaline earth metals (such as magnesium, calcium), and aluminium. Alkali metal hydroxides are preferred.

In another embodiment, the base is a metal hydride. Suitable metals include alkali metals (such as sodium, potassium, lithium), alkaline earth metals (such as magnesium, calcium), copper and aluminium. Alkali metal hydrides are preferred.

In another embodiment, the base is a metal acetate. Suitable metals include alkali metals (such as sodium, potassium), alkaline earth metals (such as magnesium, barium), and aluminium. Alkali metal acetates are preferred.

In another embodiment, the base is (aqueous) ammonia. In another embodiment, the base is an amine of formula $NR^5R^6R^7$. Suitable amines include:

primary amines, i.e. compounds of formula $NR^5R^6R^7$ in which $R^5=R^6=H$ and $R^7$ is as defined above, such as ethylamine, propylamine, butylamine, isobutylamine, amylamine, ethanolamine, cyclohexylamine;

secondary amines, i.e. compounds of formula $NR^5R^6R^7$ in which $R^5=H$ and $R^6$ and $R^7$ are as defined above (including the $NR^6R^7$ heterocycles), such as diethylamine, diisopropylamine, dibutylamine, diisobutylamine, piperidine, piperazine, morpholine; and tertiary amines, such as triethylamine, tripropylamine, tributylamine, triamylamine.

Preferably, the amine is a compound of formula $NR^5R^6R^7$ in which $R^5$, $R^6$ and $R^7$ each independently represent H or a $(C_1-C_6)$alkyl optionally substituted by a hydroxyl (and at least one of $R^5$, $R^6$ and $R^7$ is not H); or $R^5$ is H and $R^6$ and $R^7$ form, together with the nitrogen atom to which they are bonded, a 5- to 7-membered saturated heterocycle which may optionally contain another heteroatom selected from O and N. More preferably, the amine is a compound of formula $NR^5R^6R^7$ in which $R^5$, $R^6$ and $R^7$ each independently represent H or a $(C_1-C_6)$alkyl (and at least one of $R^5$, $R^6$ and $R^7$ is not H). Even more preferably, the amine is a compound of formula $NR^5R^6R^7$ in which $R^5$ is H or a $(C_1-C_4)$alkyl and $R^6$ and $R^7$ each independently represent a $(C_1-C_4)$alkyl. Tri$(C_1-C_4)$alkylamines, such as triethylamine, are especially preferred.

The base used to react with the compound of formula (II) is preferably a metal carbonate, ammonia, or an amine $NR^5R^6R^7$.

The reaction can be carried out in a solvent, at a temperature between room temperature and the reflux temperature of the solvent. Suitable solvents include methanol, ethanol, 2-propanol, dichloromethane, tetrahydrofuran, 2-methyltetrahydrofuran, 1,4-dioxane, toluene, xylene, chlorobenzene, 1,2-dichlorobenzene, acetonitrile, dimethyl sulphoxide, dimethylformamide, N-methylpyrrolidin-2-one, pyridine and water, and mixtures thereof. If the base used is also known as a solvent (e.g. diisopropylamine or triethylamine), it may be possible to carry out the reaction without any additional solvent.

The compound of formula (II) can be obtained by conversion of the keto group in position 3 of a compound of formula (III) into an enol ether:

(III)

wherein $R^2$ and $R^3$ are as defined above. This allows the group $OR^1$ to be introduced at position 3.

The conversion of compound (III) can be carried out by methods known in the art, using e.g. a tri$(C_1-C_4)$alkylorthoformate/p-toluenesulphonic acid mixture in a solvent, or a di$(C_1-C_4)$alkoxypropane/pyridinium p-toluenesulphonate mixture, at a temperature between room temperature and the reflux temperature of the solvent or of the di$(C_1-C_4)$alkoxypropane (see e.g. EP-A-201452 and Arzneim. Forsch. 1986, 36(1), 781-783). Suitable solvents include those mentioned above for the reaction of compound (II) with a base.

In one embodiment of the invention, the conversion of compound (III) into compound (II) and the reaction of the latter with the base can be carried out as a 'one pot reaction', i.e. the compound (II) resulting from the conversion of compound (III) is not isolated and the base is directly added to the reaction mixture. In this embodiment, the solvent used for the conversion reaction may be used as the solvent for the subsequent reaction with the base.

Compound (III) can be obtained by acylation of the corresponding 15-hydroxy-18-$R^2$-estr-4-en-3,17-dione by conventional methods well known to those skilled in the art, which 15-hydroxy-dione compound can in turn be obtained by microbiological hydroxylation of the corresponding 18-$R^2$-estr-4-en-3,17-dione as described e.g. in U.S. Pat. No. 4,081,537.

In one alternative, the compound of formula (I) can be obtained by conversion of the keto group in position 3 of a compound of formula (IV) into an enol ether:

(IV)

wherein $R^2$ is as defined above. This allows the group $OR^1$ to be introduced at position 3.

The conversion of compound (IV) can be carried out by methods known in the art, using e.g. a tri($C_1$-$C_4$)alkylorthoformate/p-toluenesulphonic acid mixture in a solvent, or a di($C_1$-$C_4$)alkoxypropane/pyridinium p-toluenesulphonate mixture, at a temperature between room temperature and the reflux temperature of the solvent or of the di($C_1$-$C_4$)alkoxypropane (see e.g. EP-A-201456 and Arzneim. Forsch. 1986, 36(1), 781-783). Suitable solvents include those mentioned above for the reaction of compound (II) with a base.

Compound (IV) can be obtained by reaction of compound (III) with a base under the same conditions as those described above for the reaction of compound (II) with a base.

The base used for the conversion of compound (II) or the conversion of compound (III)—depending upon the route chosen—is generally used in an amount in the range of from about 0.5 to about 10 equivalents, preferably from about 0.5 to about 8 equivalents, more preferably from about 0.5 to about 5 equivalents, and even more preferably from about 1 to about 5 equivalents, of the starting material.

FIGS. 1a-1d show the HPLC profile at 240 nm of 3-ethoxy-18-methyl-estra-3,5,15-trien-17-one, a compound obtained by conversion of 15α-acetoxy-18-methyl-estr-4-en-3,17-dione using triethylamine (FIG. 1a), potassium carbonate (FIG. 1b), butylamine (FIG. 1c) or cyclohexylamine (FIG. 1d) as the base. As can be seen from these figures, a product with a high purity profile is obtained irrespective of the base used (the main peak corresponding to said product corresponds to an elution time of about 15 min).

Compound (I) where $R^2$ is methyl can subsequently be converted into gestodene with an excellent overall yield (starting from compound (III)).

According to a second aspect, the invention therefore relates to a process for the preparation of 17-alpha-ethynyl-17-beta-hydroxy-18-methyl-estra-4,15-dien-3-one (gestodene) of the formula:

which comprises:
a) the reaction of a compound of formula (IIa) with a base:

(IIa)

wherein $R^1$ and $R^3$ are as defined above;
b) the ethynylation of the resulting compound of formula (Ia):

(Ia)

wherein $R^1$ is as defined above; and
c) the hydrolysis of the resulting compound of formula (Va):

(Va)

wherein $R^1$ is as defined above.

Step a) can be carried out under the reaction conditions described above for the preparation of the compound of formula (I).

In step b), the ethynylation of compound (Ia) can be carried out by means of treatment with a suitable ethynylating agent such as ethynylmagnesium bromide (as described e.g. in DE-A-2546062) or with other ethynylating agents such as acetylene in butyllithium or lithium acetylide complexed with ethylenediamine in tetrahydrofuran.

In step c), hydrolysis of compound (IVa) can be carried out by conventional means, e.g. treatment with an acidic solution, preferably a hydrochloric acid solution.

In one embodiment, steps b) and c) can be carried out as a 'one pot reaction'.

Compound (IIa) can be obtained from compound (IIIa):

(IIIa)

as described above for the conversion of compound (III) into compound (II).

In one alternative, step a) comprises the conversion of the keto group in position 3 of a compound of formula (IVa) into an enol ether, which allows the group $OR^1$ to be introduced at position 3:

(IVa)

This step can be carried out as described above for the conversion of the keto group of compound (IV). Compound (IVa) can be obtained by reaction of compound (IIIa) with a base as described above for the reaction of compound (III) with a base.

In one embodiment, gestodene as obtained at the end of step c) is purified by conventional means, for example by recrystallization from a suitable solvent such as a ketone (e.g. acetone), an alkane (e.g. cyclohexane), an ester (e.g. ethyl acetate), an alcohol (e.g. ethanol), water and mixtures thereof. Excellent recrystallization yields (of at least 70%, and typically in the range of from 70% to 90%) are obtained using ethanol or an ethanol/water mixture in a volume ratio of from about 1/1 to about 10/1, preferably from about 1/1 to about 5/1.

The process of the invention makes it possible to obtain gestodene, starting from compound (Ia), in yields which are generally of about 70%. The overall molecular yield, starting from compound (IIIa), is generally of about 60%.

It is noteworthy that reproducible results in terms of both yield and purity are obtained whether gestodene is prepared at the laboratory scale (example 12) or at the semi-industrial scale (example 13).

Figure 2:
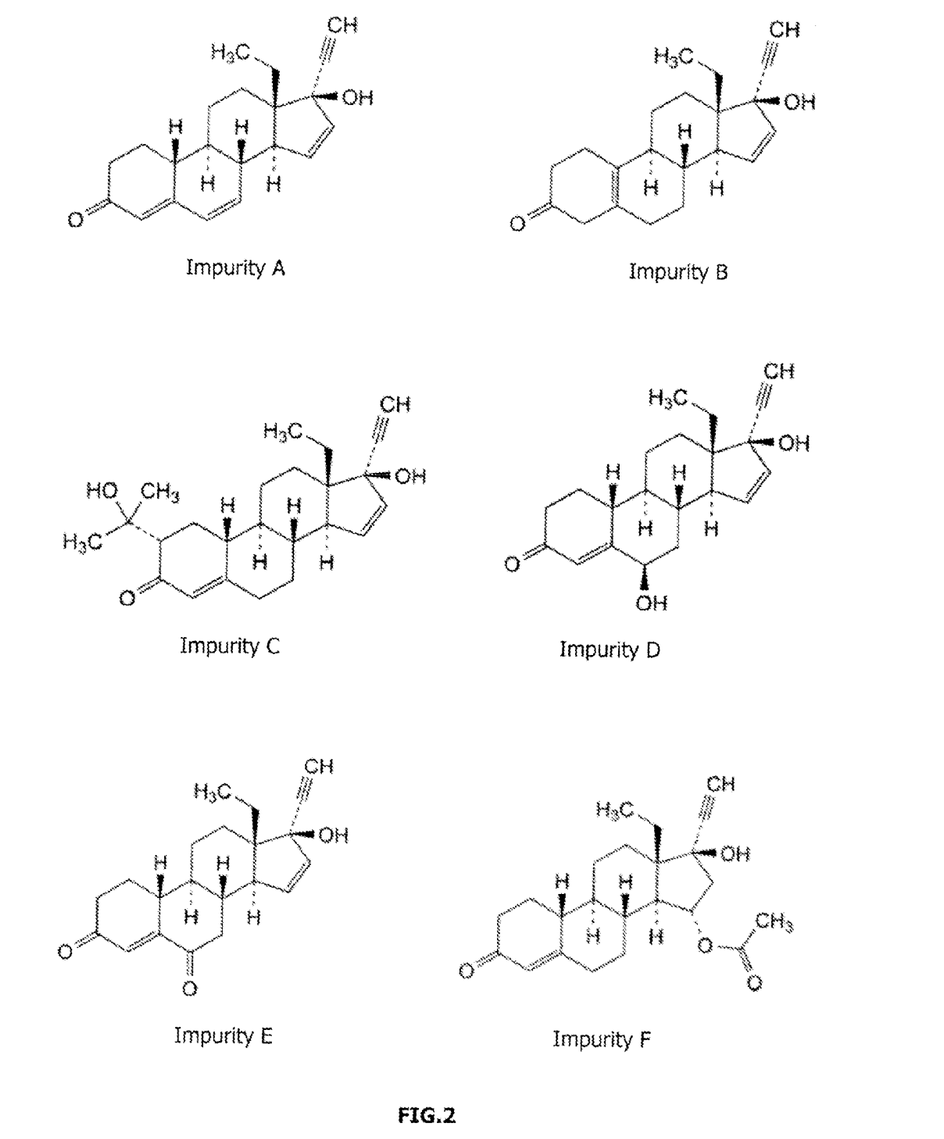
FIG. 2 shows the structure of impurities A to L that can be detected in pharmaceutical grade gestodene according to the European Pharmacopoeia.

According to the European Pharmacopoeia, pharmaceutical grade gestodene may contain impurities, denoted impurities A to L (the structure of which is shown in FIG. 2).

Batches of crude and purified gestodene obtained by the process of the invention, as detailed in examples 12 and 13, were tested for impurities. The results shown in table 1 reflect the content of each known impurity (A to L) found in the batches of crude and purified gestodene. The values for the 'unspecified impurities' are those determined on batches of purified gestodene. Unspecified impurities include impurities not known in the Pharmacopoeia and impurities known in the Pharmacopoeia but for which no relative retention time is indicated.

The process for synthesizing gestodene described by Hofmeister (Arzneim. Forsch. 1986, 36(1), 781-783) was repeated (see comparative examples 1 and 2). The resulting gestodene was tested for impurities. The results are shown in table 2.

TABLE 1

| Related substances | European Pharmacopoeia Limits at each corresponding λ max | | Gestodene batches | | | | | |
|---|---|---|---|---|---|---|---|---|
| | | | Batch 1 | Batch 2 | Batch 3 | Batch 4 | Batch 5 | Batch 6 |
| Impurity A | ≤0.3% | (254 nm) | ≤0.05% | 0.06% | ≤0.05% | ≤0.05% | ≤0.05% | ≤0.05% |
| Impurity B | ≤0.2% | (205 nm) | ≤0.05% | ≤0.05% | ≤0.05% | 0.07% | ≤0.05% | 0.06% |
| Impurity C | ≤0.2% | (254 nm) | ND | ND | ND | ND | ND | ND |
| Impurity D | ≤0.10% | (254 nm) | ≤0.05% | ≤0.05% | ≤0.05% | ≤0.05% | ≤0.05% | ≤0.05% |
| Impurity E | ≤0.10% | (254 nm) | ≤0.05% | ≤0.05% | ≤0.05% | ≤0.05% | ≤0.05% | ≤0.05% |
| Impurity F | ≤0.10% | (254 nm) | ≤0.05% | ≤0.05% | ≤0.05% | ≤0.05% | ≤0.05% | ≤0.05% |
| Impurity G | ≤0.10% | (205 nm) | ND | ND | ND | ND | ND | ND |
| Impurity H | ≤0.10% | (254 nm) | ≤0.05% | ≤0.05% | ≤0.05% | ≤0.05% | ≤0.05% | ≤0.05% |
| Impurity I | ≤0.15% | (205 nm) | ND | ND | ND | ND | ND | ND |
| Impurity J | ≤0.10% | (205 nm) | ND | ND | ND | ND | ND | ND |
| Impurity K | ≤0.10% | (205 nm) | ≤0.05% | ≤0.05% | ≤0.05% | ≤0.05% | ≤0.05% | ≤0.05% |
| Impurity L | ≤0.15% | (205 nm) | ≤0.05% | ≤0.05% | ≤0.05% | ≤0.05% | ≤0.05% | ≤0.05% |
| Any unspecified impurity | ≤0.10% | (205 or 254 nm) | ≤0.05% | ≤0.05% | ≤0.05% | ≤0.05% | ≤0.05% | 0.09% |
| Total of impurities | ≤0.5% | (254 nm) | ≤0.05% | 0.06% | ≤0.05% | ≤0.05% | ≤0.05% | ≤0.05% |

ND = not detected

TABLE 2

| Related substances | European Pharmacopoeia Limits at each corresponding λ max | | Comp Ex 1 Step c | Comp Ex 2 |
|---|---|---|---|---|
| Impurity A | ≤0.3% | (254 nm) | ≤0.05% | ≤0.05% |
| Impurity B | ≤0.2% | (205 nm) | 0.52% | 0.23% |
| Impurity C | ≤0.2% | (254 nm) | ≤0.05% | ≤0.05% |
| Impurity D | ≤0.10% | (254 nm) | 0.11% | ≤0.05% |
| Impurity E | ≤0.10% | (254 nm) | ≤0.05% | ≤0.05% |
| Impurity F | ≤0.10% | (254 nm) | 0.17% | 0.08% |
| Impurity G* | ≤0.10% | (205 nm) | ≤0.07%* | ≤0.05% |
| Impurity H* | ≤0.10% | (254 nm) | ≤0.11%* | ≤0.05% |
| Impurity I | ≤0.15% | (205 nm) | ≤0.05% | ≤0.05% |
| Impurity J* | ≤0.10% | (205 nm) | ≤0.07%* | ≤0.05% |
| Impurity K* | ≤0.10% | (205 nm) | ≤0.07%* | ≤0.05% |
| Impurity L | ≤0.15% | (205 nm) | 0.06% | ≤0.05% |
| Any unspecified impurity | ≤0.10% | (205 or 254 nm) | 0.11% | 0.08% |
| Total of impurities | ≤0.5% | (254 nm) | 0.39% | 0.08% |

Figure 3A:
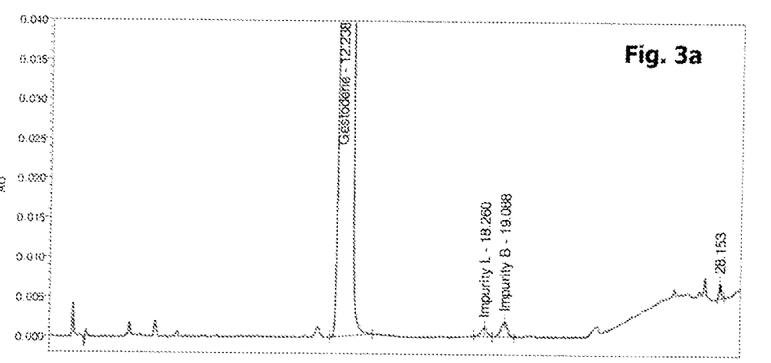
FIGS. 3a-3c show the HPLC profile at 205 nm of gestodene prepared by the process of the invention and by the Hofmeister process.
Figure 4A:
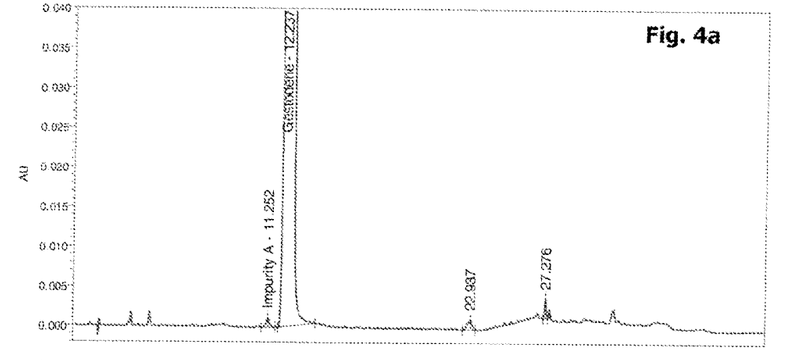
FIGS. 4a-4c show the HPLC profile at 254 nm of gestodene prepared by the process of the invention and by the Hofmeister process.

*relative retention time is not indicated in the European Pharmacopoeia; the values correspond to the highest level of impurity found at the indicated wave length As can be seen from table 1 and FIGS. 3a and 4a, the process of the invention makes it possible to obtain crude and purified gestodene (batch 1 to 6) which (i) contains impurities A, B, D, E, F, H, K and L in amounts well below the limits mentioned in the European Pharmacopoeia and (ii) is devoid of impurities C, G, I and J. Crude gestodene also contains 'unspecified impurities' in amounts which may be greater than 0.10%. These unspecified impurities are reduced to a level strictly below 0.10% after purification, in particular after recrystallization from a suitable solvent. One such unspecified impurity identified has the following structure:

Therefore, pharmaceutical grade gestodene is advantageously obtained by the process of the invention.

On the other hand, the process described by Hofmeister provides gestodene in comparable overall yield (64% vs 63% for the claimed process) starting from compound (III). However the quality of crude and purified gestodene obtained by the Hofmeister process, as determined by HPLC, was significantly lower, and purified gestodene was not of pharmaceutical grade (see table 2, comparative example 1, and FIGS. 3b and 4b). A supplementary crystallization was necessary to obtain pharmaceutical grade gestodene (see table 2, comparative example 2, and FIGS. 3c and 4c). This additional crystallisation step however resulted in a drop of the overall yield to 46%, which is significantly lower than the yield obtained with the process of the invention. This also implies that the process of the present invention is more economical than the Hofmeister process (one purification step less hence less chemicals to use and to dispose of), which will result in substantial savings on the industrial manufacturing scale.

The operating conditions used in the processes described above make it possible to introduce a double bond into position 15,16 of other steroids.

Another aspect of the invention therefore relates to a process for introducing a double bond into position 15,16 of a steroid of formula (VI):

(VI)

in which $R^a$ is H or methyl, $R^b$ is H, methyl or ethyl, preferably methyl or ethyl, and X is =O, =N(OH) or =CR$^c$R$^d$ where $R^c$ and $R^d$ each independently represent H or (C$_1$-C$_4$) alkyl, preferably =O;

which comprises the reaction of a compound of formula (VII) with a base:

(VII)

wherein $R^a$, $R^b$ and X are as defined above and $R^3$ is as defined above for compound (II).

This reaction can be carried out under the conditions described above for the preparation of the compound of formula (I). Compounds (VII) are either described in the literature or can be prepared according to methods known in the art.

In one embodiment, rings A and B of the steroid (bearing substituent $R^a$) can be represented by one of the formulae below:

wherein R is OH, (C$_1$-C$_4$)alkoxy, =O or =NOH; R' is OH or (C$_1$-C$_4$)alkoxy; each R" is independently (C$_1$-C$_4$)alkoxy or both groups together form a cyclic ketal (such as for example a 2',2'-dimethyl-1',3'-propylenedioxy group); and Z is H, OH or halogen. In the above structures, R is preferably (C$_1$-C$_4$) alkoxy or =O.

In another embodiment, rings A and B of the steroid can be represented by one of the formulae below:

-continued wherein R is OH, ($C_1$-$C_4$)alkoxy, =O or =NOH, and R' is OH or ($C_1$-$C_4$)alkoxy.

In another embodiment, rings A and B of the steroid can be represented by one of the formulae below:

wherein R, R' and Z are as defined above.

Rings A and B can optionally be substituted in positions 1, 2, 4, 6 and/or 7 by a ($C_1$-$C_4$)alkyl, preferably a methyl. Ring A can also bear a 1,2 methylene substituent. Ring B can also be substituted with a hydroxy in position 6 or 7, or with a halogen atom in position 6 or 9.

Ring C can optionally be substituted in position 11 by a ($C_1$-$C_4$)alkyl, a phenyl, a hydroxy or an oxo group.

The invention is illustrated by the following non-limiting examples in which the following abbreviations and trade names are used:
Celite® Filtration agent
EtOH Ethanol
h Hour
MeOH Methanol
2-MeTHF 2-Methyltetrahydrofuran
min Minute
mp Melting point
Norit® SX Ultra Activated carbon
THF Tetrahydrofuran Melting points were measured using a Büchi B-545 apparatus.

$^1$H Nuclear magnetic resonance (NMR) spectra were measured using a Bruker AC 200 spectrometer; spectra were run at 200 MHz in $CDCl_3$. Characteristic chemical shifts (δ) are given in parts-per-million using conventional abbreviations for designation of major peaks: s, singlet; d, doublet; dd, double doublet; t, triplet; q, quartet; m, multiplet; bs, broad singlet.

Specific optical rotation was determined on a Perkin Elmer Polarimeter 343.

HPLC analysis of 3-ethoxy-18-methyl-estra-3,5,15-trien-17-one was performed on an Agilent 1100 Series apparatus under the following conditions:

Column: Lichrospher 100 RP 18 ec 4.0×250 mm 5 μm
Mobile phase: Acetonitrile/Water 80:20 (V/V) with 10 μl of triethylamine for one liter of mobile phase
Flow. 0.8 ml/min
Injection: 10 μl.

HPLC analysis of gestodene was performed on an Agilent 1100 Series apparatus. The operating conditions were as described in the European Pharmacopoeia (see monograph July/2009: 1726).

EXAMPLE 1

15α-acetoxy-3-ethoxy-18-methyl-estra-3,5-dien-17-one

Triethyl orthoformate (30 ml, 180 mmol) and p-Toluenesulfonic acid (300 mg, 1.57 mmol) were added to a suspension of 15α-acetoxy-18-methyl-estr-4-en-3,17-dione (30 g, 87 mmol) in EtOH (180 ml). The mixture was stirred at room temperature for 1 h, and then cooled to 0° C. The precipitate was filtered, washed with cooled ethanol and dried under vacuum to afford 15α-acetoxy-3-ethoxy-18-methyl-estra-3,5-dien-17-one (31.5 g, yield: 97%).

mp: 189° C.; $^1$H-NMR δ=0.70 (t, 3H), 0.9-2.4 (m, 17H), 1.25 (t, 3H), 2.0 (s, 3H), 3.10 (dd, 1H), 3.70 (q, 2H), 5.10 (s, 1H), 5.20(m, 2H).

EXAMPLE 2

3-ethoxy-18-methyl-estra-3,5,15-trien-17-one

Triethyl orthoformate (5 ml, 30 mmol) and p-Toluenesulfonic acid (25 mg, 0.13 mmol) were added to a suspension of 15α-acetoxy-18-methyl-estr-4-en-3,17-dione (5 g, 14.5 mmol) in EtOH (40 ml). The mixture was stirred at room temperature for 1 h. Triethylamine (5 ml, 35.9 mmol) was added, and the mixture was heated under reflux for 1 h, cooled to room temperature and water (30 ml) was then added. The precipitate was filtered, washed with water and dried under vacuum to afford 3-ethoxy-18-methyl-estra-3,5,15-trien-17-one (4 g, yield: 88%).

mp: 137° C.; $^1$H-NMR δ=0.75 (t, 3H), 0.9-2.6 (m, 16H), 1.25 (t, 3H), 3.70 (m, 2H), 5.15 (s, 1H), 5.25 (d, 1H), 5.95 (m, 1H), 7.45 (d, 1H).

EXAMPLE 3

3-ethoxy-18-methyl-estra-3,5,15-trien-17-one

Triethyl orthoformate (5 ml, 30 mmol) and p-Toluenesulfonic acid (50 mg, 0.26 mmol) were added to a suspension of 15α-acetoxy-18-methyl-estr-4-en-3,17-dione (5 g, 14.5 mmol) in EtOH (30 ml). The mixture was stirred at room temperature for 1 h. Triethylamine (2 ml, 14.4 mmol) was added, and the mixture was heated under reflux for 3 h, cooled to 10° C. and water (15 ml) was then added. The precipitate was filtered, washed with water and dried. The crude product was purified by flash chromatography, eluting with heptane and ethyl acetate (7:3), crystallized from heptane, and dried under vacuum to afford 3-ethoxy-18-methyl-estra-3,5,15-trien-17-one (2.8 g, yield: 62%).

mp: 137° C.; the $^1$H-NMR spectrum was in accordance with that obtained for example 2.

EXAMPLE 4

3-ethoxy-18-methyl-estra-3,5,15-trien-17-one

Triethyl orthoformate (5 ml, 30 mmol) and p-Toluenesulfonic acid (50 mg, 0.26 mmol) were added to a suspension of 15α-acetoxy-18-methyl-estr-4-en-3,17-dione (5 g, 14.5 mmol) in EtOH (30 ml). The mixture was stirred at room temperature for 1 h. Diisopropylamine (6.3 ml, 36 mmol) was added, and the mixture was heated under reflux for 2 h, cooled to 10° C. and water (15 ml) was then added. The precipitate was filtered, washed with water and dried. The crude product was purified by flash chromatography, eluting with heptane and ethyl acetate (7:3), crystallized from heptane, and dried under vacuum to afford 3-ethoxy-18-methyl-estra-3,5,15-trien-17-one (3.18 g, yield: 71%).

mp: 136° C.; the $^1$H-NMR spectrum was in accordance with that obtained for example 2.

EXAMPLE 5

3-ethoxy-18-methyl-estra-3,5,15-trien-17-one

Triethyl orthoformate (3 ml, 18 mmol) and p-Toluenesulfonic acid (30 mg, 0.16 mmol) were added to a suspension of 15α-acetoxy-18-methyl-estr-4-en-3,17-dione (3 g, 8.8 mmol) in EtOH (18 ml). The mixture was stirred at room temperature for 1 h. Butylamine (3.6 ml, 35 mmol) was added, and the mixture was heated at 40° C. for 2 h, cooled to 10° C. and water (15 ml) was then added. The precipitate was filtered, washed with water and dried under vacuum to afford 3-ethoxy-18-methyl-estra-3,5,15-trien-17-one (2.6 g, yield: 94%).

mp: 132° C.; the $^1$H-NMR spectrum was in accordance with that obtained for example 2.

EXAMPLE 6

3-ethoxy-18-methyl-estra-3,5,15-trien-17-one

Triethyl orthoformate (0.6 ml, 3.6 mmol) and p-Toluenesulfonic acid (6 mg, 0.032 mmol) were added to a suspension of 15α-benzoyloxy-18-methyl-estr-4-en-3,17-dione (0.6 g, 1.5 mmol) in EtOH (5 ml). The mixture was stirred at room temperature for 1 h. Triethylamine (1 ml, 7.2 mmol) was added, and the mixture was heated under reflux for 30 min, cooled to room temperature and water (50 ml) was then added. The precipitate was filtered, washed with water and dried. The crude product was purified by flash chromatography, eluting with heptane and ethyl acetate (7:3), crystallized from heptane, and dried under vacuum to afford 3-ethoxy-18-methyl-estra-3,5,15-trien-17-one (0.23 g, yield: 50%).

The $^1$H-NMR spectrum was in accordance with that obtained for example 2.

EXAMPLE 7

3-ethoxy-18-methyl-estra-3,5,15-trien-17-one

Triethyl orthoformate (3 ml, 18 mmol) and p-Toluenesulfonic acid (30 mg, 0.16 mmol) were added to a suspension of 15α-acetoxy-18-methyl-estr-4-en-3,17-dione (3 g, 8.8 mmol) in EtOH (18 ml). The mixture was stirred at room temperature for 1 h. Ammonia 32% (15.4 ml, 145 mmol) was added, and the mixture was heated at 40° C. for 48 h, cooled to 10° C., and ethyl acetate and water (15 ml) were then added. The extract was washed with water and concentrated. The crude product was purified by flash chromatography, eluting with heptane and ethyl acetate (8:2), crystallized from heptane, and dried under vacuum to afford 3-ethoxy-18-methyl-estra-3,5,15-trien-17-one (1.54 g, yield: 56%).

The $^1$H-NMR spectrum was in accordance with that obtained for example 2.

EXAMPLE 8

3-methoxy-18-methyl-estra-3,5,15-trien-17-one a) 15α-acetoxy-3-methoxy-18-methyl-estra-3,5-dien-17-one Pyridinium p-Toluenesulfonate (260 mg, 1.03 mmol) was added to a suspension of 15α-acetoxy-18-methyl-estr-4-en-3,17-dione (2 g, 5.8 mmol) in 2,2-dimethoxypropane (20 ml). The mixture was stirred under reflux for 7 h and at room temperature overnight. It was then cooled to −10° C. for 1 h. The precipitate was filtered, washed with cooled MeOH and dried under vacuum to afford 15α-acetoxy-3-methoxy-18-methyl-estra-3,5-dien-17-one (1.84 g, yield: 88%).

$^1$H-NMR δ=0.70 (t, 3H), 1.5-2.5 (m, 21H), 3.10 (dd, 1H), 3.50 (s, 3H), 5.15 (s, 1H), 5.25 (m, 1H).

b) 3-methoxy-18-methyl-estra-3,5,15-trien-17-one

A mixture of 15α-acetoxy-3-methoxy-18-methyl-estra-3,5-dien-17-one (1 g, 2.8 mmol) in suspension in a 1/1 MeOH/water solution (20 ml), and potassium carbonate (1 g, 7.23 mmol) was heated at 50° C. for 1 h. The mixture was allowed to cool to room temperature and the precipitate was filtered, washed with water and dried under vacuum to afford 3-methoxy-18-methyl-estra-3,5,15-trien-17-one (0.67 g, yield: 80%). mp: 159-161° C.; $^1$H-NMR δ=0.72 (t, 3H), 0.9-2.4 (m, 16H), 3.55 (s, 3H), 5.18 (s, 1H), 5.28 (d, 1H), 5.95 (m, 1H), 7.45 (d, 1H).

EXAMPLE 9

3-ethoxy-18-methyl-estra-3,5,15-trien-17-one

Triethylamine (2 ml, 14.4 mmol) was added to a suspension of 15α-acetoxy-3-ethoxy-18-methyl-estr-3,5-dien-17-one (2 g, 5.4 mmol) in DMF (20 ml). The mixture was stirred at 40° C. for 3 days, cooled to 10° C. and water (15 ml) was then added. The precipitate was filtered and washed with water. The crude product was purified by flash chromatography, eluting with heptane and ethyl acetate (7:3), crystallized from heptane, and dried under vacuum to afford 3-ethoxy-18-methyl-estra-3,5,15-trien-17-one (1.2 g, yield: 66%).

mp: 139° C.; the $^1$H-NMR spectrum was in accordance with that obtained for example 2.

EXAMPLE 10

18-methyl-estra-4,15-dien-3,17-dione

Triethylamine (4 ml, 28.7 mmol) was added to a suspension of 15α-acetoxy-18-methyl-estr-4-en-3,17-dione (4 g, 11.6 mmol) in EtOH (24 ml). The mixture was heated under reflux for 2 h. It was cooled to room temperature and water (50 ml) was added. The precipitate was filtered, washed with a 6/4 EtOH/water solution and dried under vacuum. The residue was purified by flash chromatography on silica gel to afford 18-methyl-estra-4,15-dien-3,17-dione (2 g, yield: 62%).

mp: 155-157° C.; $^1$H-NMR δ=0.6 (t, 3H), 0.7-2.5 (m, 18H), 5.65 (s, 1H), 5.85 (m, 1H), 7.30 (dd, 1H).

EXAMPLE 11

18-methyl-estra-4,15-dien-17-one

Potassium carbonate (0.6 g, 4.4 mmol) was added to a suspension of 15α-acetoxy-18-methyl-estr-4-en-3,17-dione (3 g, 8.7 mmol) in methanol (27 ml) and the mixture was heated at 40° C. for 1 h. The mixture was allowed to cool to room temperature and water (100 ml) was then added. The precipitate was filtered, washed with water and dried under vacuum, to afford 18-methyl-estra-4,15-dien-3,17-dione (1.7 g, yield: 70%).

mp: 155-157° C.; the $^1$H-NMR spectrum was in accordance with that obtained for example 10.

EXAMPLE 12

17α-ethynyl-17β-hydroxy-18-methyl-estra-4,15-dien-3-one a) 3-ethoxy-18-methyl-estra-3,5,15-trien-17-one Triethyl orthoformate (15 ml, 90.3 mmol) and p-Toluenesulfonic acid (250 mg, 1.31 mmol) were added to a suspension of 15α-acetoxy-18-methyl-estr-4-en-3,17-dione (25 g, 72.7 mmol) in EtOH (150 ml). The mixture was stirred at room temperature for 1 h. Triethylamine (25 ml, 179.4 mmol) was added. The mixture was heated under reflux for 2 h, cooled to 5° C. and water (75 ml) was then added. The precipitate was filtered, washed with a 1/1 EtOH/water solution and dried under vacuum to afford 3-ethoxy-18-methyl-estra-3,5,15-trien-17-one (20 g, yield: 88%).

mp: 138-139° C.; $^1$H-NMR δ=0.75 (t, 3H), 0.9-2.6 (m, 16H), 1.25 (t, 3H), 3.70 (m, 2H), 5.15 (s, 1H), 5.25 (d, 1H), 5.95 (m, 1H), 7.45 (d, 1H).

b) 17α-ethynyl-17β-hydroxy-18-methyl-estra-4,15-dien-3-one

A 0.5 M solution of ethynylmagnesium bromide in THF (200 ml, 100 mmol) was added under a nitrogen atmosphere to a solution of 3-ethoxy-18-methyl-estra-3,5,15-trien-17-one (20 g, 64.1 mmol) in 2-MeTHF (40 ml) without exceeding 25° C. The mixture was stirred at room temperature for 2 h, cooled to 7° C. and EtOH (10 ml) was added. The mixture was stirred for 10 min, 3N aqueous hydrochloric acid solution was then added, and the mixture was stirred at a temperature below 10° C. for 2 h. The organic layer was separated and the aqueous layer was extracted with 2-MeTHF. The organic layers were combined and successively washed with 10% aqueous sodium chloride solution, 10% aqueous sodium hydrogencarbonate solution and 10% aqueous sodium chloride solution. 1-butanol (40 ml) was added to the organic layer and THF and 2-MeTHF were evaporated under vacuum at a temperature below 50° C. The remaining mixture in 1-butanol was cooled to 5° C. The precipitate was filtered, washed with water and dried under vacuum to afford crude 17α-ethynyl-17β-hydroxy-18-methyl-estra-4,15-dien-3-one (14.9 g, yield: 75%).

$^1$H-NMR δ=0.85 (t, 3H), 1.0-2.6 (m, 18H), 2.60 (s, 1H), 2.70 (bs, 1H), 5.65 (m, 1H), 5.80 (s, 1H), 5.90 (m, 1H).

c) 17α-ethynyl-17β-hydroxy-18-methyl-estra-4,15-dien-3-one

Crude 17α-ethynyl-17β-hydroxy-18-methyl-estra-4,15-dien-3-one (5 g, 16.1 mmol) and Norit® SX ultra (0.5 g) in suspension in EtOH (50 ml) were stirred under reflux until they had completely dissolved. The hot reaction mixture was filtered over Celite®, rinsed with hot EtOH and cooled to 0° C. The precipitate was filtered, washed with EtOH and dried under vacuum to afford pure 17α-ethynyl-17β-hydroxy-18-methyl-estra-4,15-dien-3-one (4 g, yield: 80%).

mp: 197-199° C.; $^1$H-NMR δ=0.85 (t, 3H), 1.0-2.6 (m, 18H), 2.60 (s, 1H), 2.70 (bs, 1H), 5.65 (m, 1H), 5.80 (s, 1H), 5.90 (m, 1H).

EXAMPLE 13

Figure 1A:
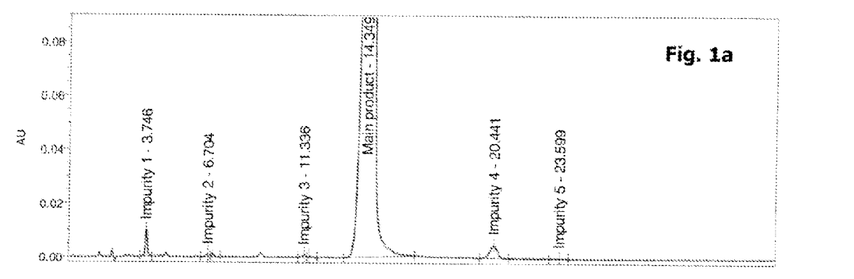
FIGS. 1a-1d show the HPLC profile of 3-ethoxy-18-methyl-estra-3,5,15-trien-17-one prepared using various bases.

17α-ethynyl-17β-hydroxy-18-methyl-estra-4,15-dien-3-one a) 3-ethoxy-18-methyl-estra-3,5,15-trien-17-one Triethyl orthoformate (1.7 l, 10.2 mol) and p-Toluenesulfonic acid (16.8 g, 88.3 mmol) were added to a suspension of 15α-acetoxy-18-methyl-estr-4-en-3,17-dione (1.7 Kg, 4.94 mol) in EtOH (11 l). The mixture was stirred at room temperature for 1 h. Triethylamine (1.7 l, 12.2 mol) was added. The mixture was heated under reflux for 2 h, cooled to 5° C. and water (5 l) was then added. The precipitate was filtered, washed with a 1/1 EtOH/water solution and dried under vacuum to afford 3-ethoxy-18-methyl-estra-3,5,15-trien-17-one (1.36 Kg, yield: 88%).

mp: 138-139° C.; $^1$H-NMR δ=0.75 (t, 3H), 0.9-2.6 (m, 16H), 1.25 (t, 3H), 3.70 (m, 2H), 5.15 (s, 1H), 5.25 (d, 1H), 5.95 (m, 1H), 7.45 (d, 1H). HPLC analysis was as shown in FIG. 1a.

b) 17α-ethynyl-17β-hydroxy-18-methyl-estra-4,15-dien-3-one

A 0.5 M solution of ethynylmagnesium bromide in THF (13.6 l, 6.8 mol) was added under a nitrogen atmosphere to a solution of 3-ethoxy-18-methyl-estra-3,5,15-trien-17-one (1.34 Kg, 4.29 mol) in 2-MeTHF (2.7 l) without exceeding 25° C. The mixture was stirred at room temperature for 2 h, cooled to 7° C. and EtOH (0.7 l) was added.

The mixture was stirred for 10 min, 2.7N aqueous hydrochloric acid solution was then added, and the mixture was stirred at a temperature below 10° C. for 2 h. The organic layer was separated and the aqueous layer was extracted with 2-MeTHF. The organic layers were combined and successively washed with 5% aqueous sodium chloride solution, 5% aqueous potassium acetate solution and 5% aqueous sodium chloride solution. 1-butanol (1.3 l) was added to the organic layer and THF and 2-MeTHF were evaporated under vacuum at a temperature below 50° C. The remaining mixture in 1-butanol was cooled to 0° C. The precipitate was filtered, washed with water and dried under vacuum to afford crude 17α-ethynyl-17β-hydroxy-18-methyl-estra-4,15-dien-3-one (1.06 kg, yield: 80%).

Purity by HPLC: >98%; $^1$H-NMR δ=0.85 (t, 3H), 1.0-2.6 (m, 18H), 2.60 (s, 1H), 2.70 (bs, 1H), 5.65 (m, 1H), 5.80 (s, 1H), 5.90 (m, 1H).

c) 17α-ethynyl-17β-hydroxy-18-methyl-estra-4,15-dien-3-one

Crude 17α-ethynyl-17β-hydroxy-18-methyl-estra-4,15-dien-3-one (1.04 Kg, 3.35 mol) and Norit® SX ultra (21 g) in suspension in a 4/1 EtOH/water solution (8.4 l) were stirred under reflux until complete dissolution. The hot reaction mixture was filtered over a cartridge filter. The cartridge filter was rinsed with hot EtOH and the reaction mixture was cooled to 0° C. The precipitate was filtered, washed with a 4/1 EtOH/water solution and dried under vacuum to afford pure 17α-ethynyl-17β-hydroxy-18-methyl-estra-4,15-dien-3-one (925 g, yield: 89%, overall yield: 63%).

mp: 197-199° C.; $[α]_D^{20}$=−191° (MeOH); $^1$H-NMR δ=0.85 (t, 3H), 1.0-2.6 (m, 18H), 2.60 (s, 1H), 2.70 (bs, 1H), 5.65 (m, 1H), 5.80 (s, 1H), 5.90 (m, 1H). HPLC analysis was as shown in FIGS. 3a and 4a.

EXAMPLE 14

6-hydroxy-18-methyl-estra-4,15-dien-3,17-dione a) 15α-acetoxy-6-hydroxy-18-methyl-estr-4-en-3,17-dione A mixture of 15α-acetoxy-3-ethoxy-18-methyl-estra-3,5-dien,17-one (3 g, 8.06 mmol) and 3-chloroperbenzoic acid (1.4 g, 8.06 mmol) in EtOH (72 ml) was stirred at room temperature for 1 h and water (100 ml) was then added. The mixture was extracted with ethyl acetate (100 ml), the organic layer was successively washed with 10% aqueous sodium bicarbonate solution and 10% aqueous sodium chloride solution, dried, and the solvent removed. The crude product was purified by flash chromatography on silica gel eluting with heptane/ethyl acetate (5/5) to afford pure 15α-acetoxy-6-hydroxy-18-methyl-estr-4-en-3,17-dione (1.37 g, yield: 47%) as an oil.

$^1$H-NMR δ=0.80 (t, 3H), 1.1-2.6 (m, 16H), 2.0 (s, 3H), 2.90 (d, 1H), 3.10 (d, 1H), 3.40 (bs, 1H), 4.10 (s, 1H), 5.20 (m, 1H), 5.80 (s, 1H).

b) 6-hydroxy-18-methyl-estr-4,15-dien-3,17-dione

Triethylamine (0.5 ml, 3.6 mmol) was added to a suspension of 15α-acetoxy-6-hydroxy-18-methyl-estr-4-en-3,17-dione (0.5 g, 1.4 mmol) in EtOH (3 ml). The mixture was heated under reflux for 2 h, cooled to room temperature and then water (30 ml) was added. The mixture was extracted with ethyl acetate (30 ml), the organic layer was washed with water (50 ml), dried and the solvent removed. The crude product was purified by flash chromatography on silica gel eluting with diisopropyl ether/ethyl acetate (7/3) to afford pure 6-hydroxy-18-methyl-estra-4,15-dien-3,17-dione (0.14 g, yield: 34%) as an oil.

$^1$H-NMR δ=0.70 (t, 3H), 0.8-2.4 (m, 17H), 3.90 (s, 1H), 5.70 (d, 1H), 5.90 (m, 1H), 7.40 (d, 1H).

EXAMPLE 15

3-hydroxy-18-methyl-estra-1,3,5(10),15-tetraen-17-one a) 15α-acetoxy-3-hydroxy-18-methyl-estra-1,3,5(10)-trien-17-one 15α-acetoxy-18-methyl-estr-4-en-3,17-dione (2.5 g, 7.3 mmol) in acetonitrile (80 ml) was added to a suspension of copper (II) bromide (3.2 g, 14.3 mmol) and lithium bromide (0.7 g, 8.0 mmol) in acetonitrile (20 ml). The mixture was stirred at room temperature for 4 h, then pyridine (2 ml) and water (300 ml) were added. The mixture was extracted with ethyl acetate (50 ml), the organic layer was washed with water (50 ml), dried and the solvent removed. The crude product was purified by flash chromatography on silica gel eluting with diisopropyl ether to afford pure 15α-acetoxy-18-methyl-estra-1,3,5(10)-triene-17-one-3-hydroxy (0.52 g, yield: 21%). mp: 99° C.; $^1$H-NMR δ=0.80 (t, 3H), 1.1-2.5 (m, 13H), 2.10 (s, 3H), 2.8 (m, 2H), 3.15 (dd, 1H), 5.35 (m, 1H), 6.55 (s, 1H), 6.65 (d, 1H), 7.15 (d, 1H).

b) 3-hydroxy-18-methyl-estra-1,3,5(10),15-tetraen-17-one

Triethylamine (0.5 ml, 3.6 mmol) was added to a suspension of 15α-acetoxy-3-hydroxy-18-methyl-estra-1,3,5(10)-trien-17-one (0.52 g, 1.5 mmol) in EtOH (7 ml). The mixture was heated under reflux for 2 h, cooled to room temperature and then water (30 ml) was added. The mixture was extracted with ethyl acetate (30 ml), the organic layer was washed with water (50 ml), dried and the solvent removed. The crude product was purified by flash chromatography on silica gel eluting with diisopropyl ether to afford pure 3-hydroxy-18-methyl-estra-1,3,5(10),15-tetraen-17-one (0.27 g, yield: 64%).

mp: 230° C., $^1$H-NMR δ=0.80 (t, 3H), 1.1-3.0 (m, 14H), 6.25 (dd, 1H), 6.60 (d, 1H), 6.70 (dd, 1H), 7.0 (d, 1H), 7.70 (dd, 1H).

EXAMPLE 16

6-chloro-18-methyl-estra-4,15-dien-3,17-dione a) 15α-acetoxy-6-chloro-18-methyl-estr-4-en-3,17-dione 15α-acetoxy-3-ethoxy-18-methyl-estra-3,5,15-trien-17-one (2 g, 5.37 mmol) in acetone (60 ml) was cooled to 5° C., then glacial acetic acid (10 ml, 174.6 mmol), potassium acetate solution (11 ml, 11.2 mmol) and N-chlorosuccinimide (1 g, 7.5 mmol) were successively added. The mixture was stirred to 5° C. for 30 min. Ice (50 g) was added. The mixture was extracted with ethyl acetate (50 ml), the organic layer was washed successively with saturated bicarbonate solution (2×50 ml), water (2×50 ml), dried and the solvent removed. The crude product was purified by flash chromatography on silica gel eluting with an ethyl acetate/ heptane (1/1) mixture to afford pure 15α-acetoxy-6-chloro-18-methyl-estra-4-en-3,17-dione (1 g, yield: 49%). mp: 115° C.; $^1$H-NMR δ=0.80 (t, 3H), 1.2-2.7 (m, 17H), 2.05 (s, 3H), 3.20 (dd, 1H), 4.80 (d, 1H), 5.25 (m, 1H), 5.95 (d, 1H).

b) 6-chloro-18-methyl-estra-4,15-dien-3,17-dione

Triethylamine (0.5 ml, 3.6 mmol) was added to a suspension of 15α-acetoxy-6-chloro-18-methyl-estra-4-en-3,17-dione (0.5 g, 1.32 mmol) in ethanol (15 ml). The mixture was stirred at 45° C. for 2 h, cooled to 10° C. and water (4 ml) was then added. The precipitate was filtered and washed with an ethanol/water (1/1) mixture. The crude product was crystallized from ethanol and dried under vacuum to afford 6-chloro-18-methyl-estra-4,15-dien-3,17-dione (0.26 g, yield: 62%).

mp: 136° C.; $^1$H-NMR δ=0.80 (t, 3H), 1.2-2.8 (m, 16H), 5.35 (s, 1H), 5.95 (d, 1H), 6.05 (dd, 1H), 7.45 (d, 1H).

EXAMPLE 17

3-ethoxy-18-methyl-estra-3,5,15-trien-17-one

Figure 1B:
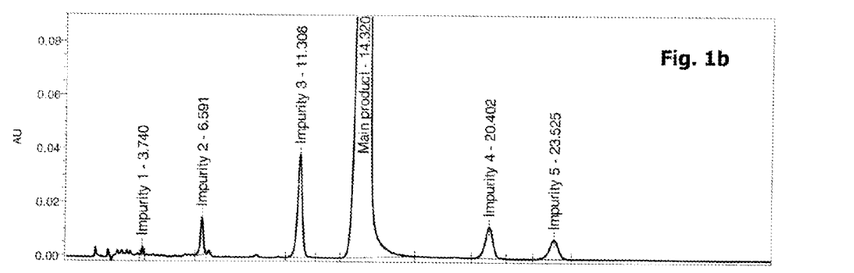

Triethyl orthoformate (2 ml, 12 mmol) and p-Toluenesulfonic acid (20 mg, 0.10 mmol) were added to a suspension of 15α-acetoxy-18-methyl-estr-4-en-3,17-dione (2 g, 5.81 mmol) in ethanol (20 ml). The mixture was stirred at room temperature for 1 h. Potassium carbonate (1.1 g, 8.06 mmol) in solution in water (20 ml) was added and the mixture was heated under reflux for 2 h, cooled to 10° C. and water (20 ml) was then added. The precipitate was filtered, washed with water and dried under vacuum, to afford 3-ethoxy-18-methyl-estra-3,5,15-trien-17-one (1.3 g, yield: 78%). mp and $^1$H-NMR were in accordance with those obtained for example 2. HPLC analysis was as shown in FIG. 1b.

EXAMPLE 18

3-ethoxy-18-methyl-estra-3,5,15-trien-17-one

Figure 1C:
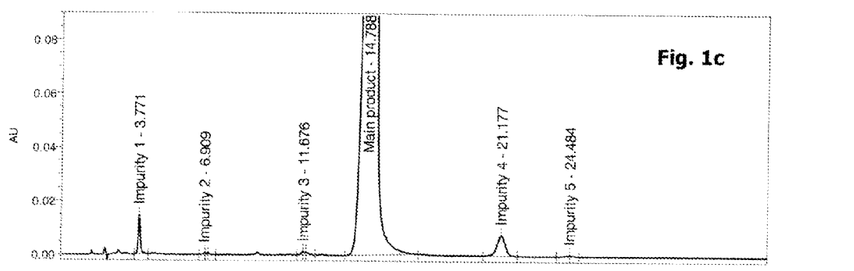

Triethyl orthoformate (3 ml, 18 mmol) and p-Toluenesulfonic acid (30 mg, 0.16 mmol) were added to a suspension of 15α-acetoxy-18-methyl-estr-4-en-3,17-dione (3 g, 8.72 mmol) in ethanol (20 ml). The mixture was stirred at room temperature for 1 h. Butylamine (1 ml, 9.72 mmol) was added and the mixture was heated at 30° C. for 2 h, cooled to 10° C. and water (10 ml) was then added. The precipitate was filtered, washed with water and dried under vacuum, to afford 3-ethoxy-18-methyl-estra-3,5,15-trien-17-one (2.2 g, yield: 88%).

mp and $^1$H-NMR were in accordance with those obtained for example 2. HPLC analysis was as shown in FIG. 1c.

EXAMPLE 19

3-ethoxy-18-methyl-estra-3,5,15-trien-17-one

Figure 1D:
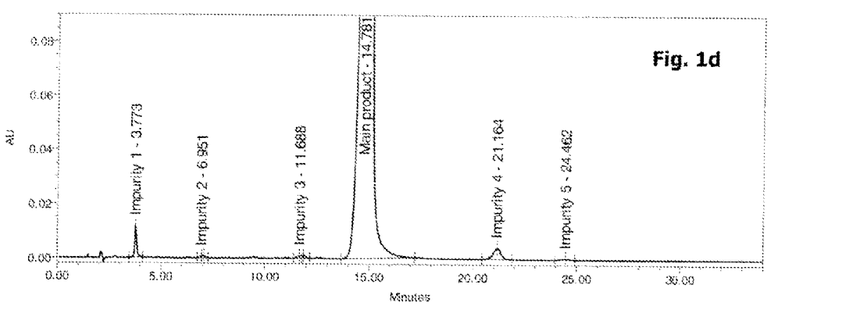

Triethyl orthoformate (3 ml, 18 mmol) and p-Toluenesulfonic acid (30 mg, 0.16 mmol) were added to a suspension of 15α-acetoxy-18-methyl-estr-4-en-3,17-dione (3 g, 8.72 mmol) in ethanol (20 ml). The mixture was stirred at room temperature for 1 h. Cyclohexylamine (1 ml, 8.75 mmol) was added and the mixture was heated at 30° C. for 2 h, cooled to 10° C. and water (20 ml) was then added. The precipitate was filtered, washed with water and dried under vacuum, to afford 3-ethoxy-18-methyl-estra-3,5,15-trien-17-one (2.0 g yield: 80%).

mp and $^1$H-NMR were in accordance with those obtained for example 2. HPLC analysis was as shown in FIG. 1d.

COMPARATIVE EXAMPLE 1

17α-ethynyl-17β-hydroxy-18-methyl-estra-4,15-dien-3-one

This compound was prepared following the method described in Arzneim. Forsch. 1986, 36(1), 781-783 (scheme 2 and steps 3.9 and 3.10).

a) 15α-acetoxy-3-methoxy-18-methyl-estra-3,5-dien-17-dione

A suspension of 15α-acetoxy-18-methyl-estr-4-en-3,17-dione (48 g, 139 mmol) and pyridinium p-Toluenesulfonate (4.8 g, 19.1 mmol) in 2,2-dimethoxypropane (400 ml) was refluxed for 6 h. The mixture was then cooled to −10° C. for 2 h. The precipitate was filtered, washed with cooled methanol and dried under vacuum to afford 15α-acetoxy-3-methoxy-18-methyl-estra-3,5-dien-17-one (42.7 g, yield: 86%).

$^1$H-NMR was in accordance with that obtained for example 8.

b) 17α-ethynyl-17β-hydroxy-18-methyl-estra-4,15-dien-3-one

A solution of 15α-acetoxy-3-methoxy-18-methyl-estra-3,5-dien-17-one (20 g, 55.8 mmol) in THF (500 ml) was added, under a nitrogen atmosphere, to a suspension of Lithium Acetylide complex (32.8 g, 356 mmol) in THF (500 ml) at 0° C. The mixture was stirred for 15 min at 0° C. Then a 5N aqueous hydrochloric acid solution (180 ml) was added and the mixture was stirred until the reaction was complete. The organic layer was separated, and the aqueous phase was extracted with ethyl acetate. The organic layers were combined, washed with water until pH =7, and concentrated to afford crude 17α-ethynyl-17β-hydroxy-18-methyl-estra-4,15-dien-3-one (21 g). Purity by HPLC: ≈70%.

c) 17α-ethynyl-17β-hydroxy-18-methyl-estra-4,15-dien-3-one

Figure 3B:
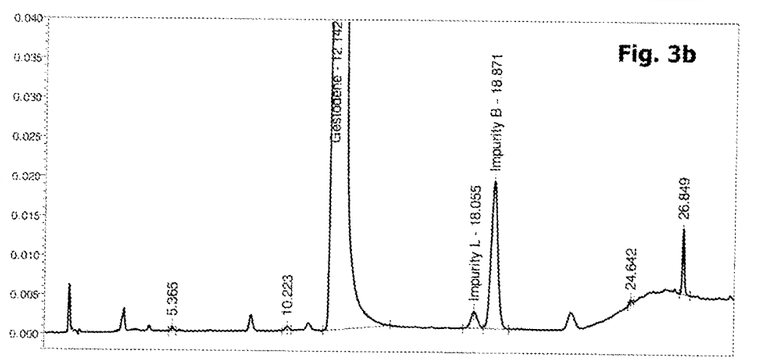
Figure 4B:
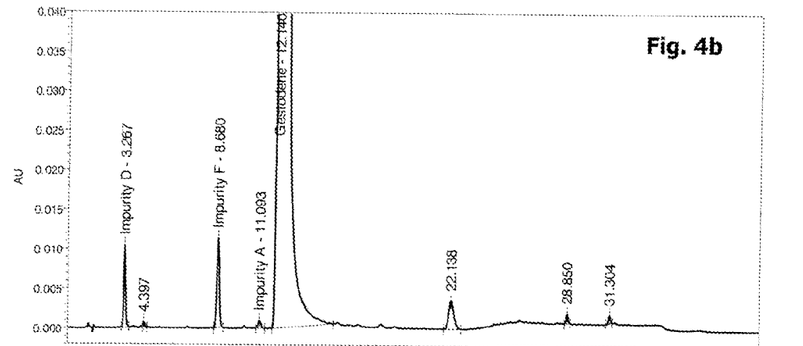

Crude 17α-ethynyl-17β-hydroxy-18-methyl-estra-4,15-dien-3-one (21 g) was dissolved in ethyl acetate (100 ml), treated with charcoal (20 g) under reflux for 10 min. The mixture was filtered through a pad of Celite® and concentrated. The product was crystallized from methanol (50 ml) and dried under vacuum to afford 17α-ethynyl-17β-hydroxy-18-methyl-estra-4,15-dien-3-one (13 g, yield: 75%, overall yield: 64%).

mp: 198° C., $^1$H-NMR was in accordance with that obtained for example 13c. HPLC analysis was as shown in FIGS. 3b and 4b.

COMPARATIVE EXAMPLE 2

17α-ethynyl-17β-hydroxy-18-methyl-estra-4,15-dien-3-one

Figure 3C:
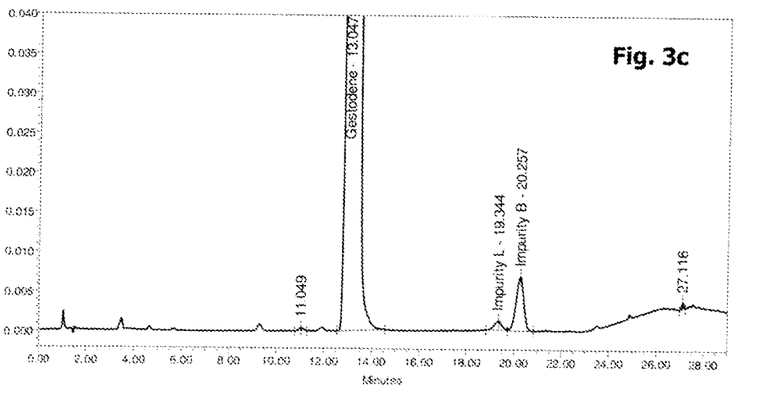
Figure 4C:
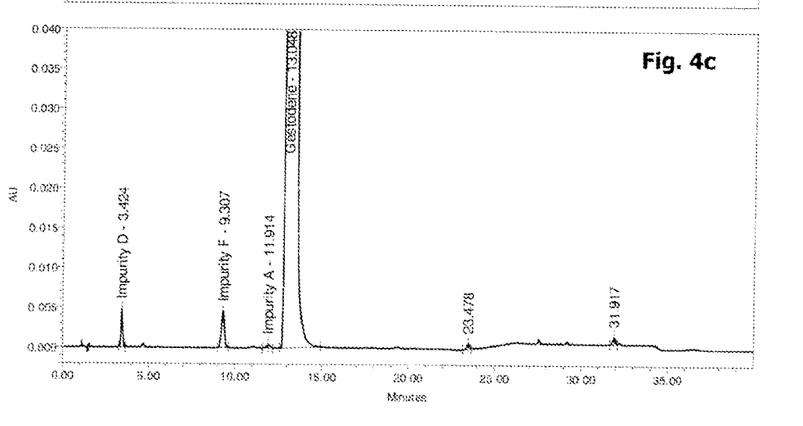

The product from comparative example 1 (11.6 g) was again crystallized from methanol (59 ml) and dried under vacuum to afford 17α-ethynyl-17β-hydroxy-18-methyl-estra-4,15-dien-3-one (8.4 g, yield: 72%, overall yield: 46%). mp: 198° C., $^1$H-NMR was in accordance with that obtained for example 13c. HPLC analysis was as shown in FIGS. 3c and 4c.

The invention claimed is:

1. A process for the preparation of 17-alpha-ethynyl-17-beta-hydroxy-18-methyl-estra-4,15-dien-3-one (gestodene) of the formula:

which comprises:

a) reacting a compound of formula (IIa):

wherein $R^1$ is a ($C_1$-$C_4$)alkyl and $R^3$ is —$COR^4$, where $R^4$ is a ($C_1$-$C_6$)alkyl, a phenyl optionally substituted with 1 to 3 ($C_1$-$C_4$)alkyl or a benzyl in which the phenyl is optionally substituted with 1 to 3 ($C_1$-$C_4$)alkyl, with a base to give a compound of formula (Ia):

wherein $R^1$ is as defined above;

b) ethynylating the compound of formula (Ia) to give a compound of formula (Va):

wherein R¹ is as defined above;

c) hydrolyzing the compound of formula (Va) to give gestodene, wherein the gestodene thus obtained has total impurities in an amount of no more than 0.5% by weight; and d) purifying gestodene as obtained in step c);

wherein the base used in step a) is selected from a metal carbonate; a metal bicarbonate; a metal hydroxide; a metal hydride; a metal acetate; ammonia; and an amine of formula NR⁵R⁶R⁷ where R⁵, R⁶ and R⁷ each independently represent H; a (C₁-C₆)alkyl optionally substituted by a hydroxyl; or a (C₃-C₆)cycloalkyl; and at least one of R⁵, R⁶ and R⁷ is not H.

2. The process according to claim 1, wherein the base is selected from a metal carbonate, ammonia and an amine of formula NR⁵R⁶R⁷.

3. The process according to claim 1, wherein the base is an amine of formula NR⁵R⁶R⁷ in which R⁵, R⁶ and R⁷ each independently represent H or a (C₁-C₆)alkyl optionally substituted by a hydroxyl; and at least one of R⁵, R⁶ and R⁷ is not H.

4. The process according to claim 1, wherein the base is an amine of formula NR⁵R⁶R⁷ in which R⁵, R⁶ and R⁷ each independently represent H or a (C₁-C₆)alkyl; and at least one of R⁵, R⁶ and R⁷ is not H.

5. The process according to claim 1, wherein the base is an amine of formula NR⁵R⁶R⁷ in which R⁵ is H or a (C₁-C₄)alkyl and R⁶ and R⁷ each independently represent a (C₁-C₄)alkyl.

6. The process according to claim 1, wherein steps b) and c) are carried out as a one pot reaction.

7. A process for the preparation of 17-alpha-ethynyl-17-beta-hydroxy-18-methyl-estra-4,15-dien-3-one (gestodene) of the formula:

which comprises:

a) converting the keto group in position 3 of a compound of formula (IIIa):

wherein R³ is —COR⁴, where R⁴ is a (C₁-C₆)alkyl, a phenyl optionally substituted with 1 to 3 (C₁-C₄) alkyl or a benzyl in which the phenyl is optionally substituted with 1 to 3 (C₁-C₄)alkyl, into an enol ether to give a compound of formula (IIa):

wherein R¹ is a (C₁-C₄)alkyl and R³ is as defined above;

b) reacting the compound of formula (IIa) with a base to give a compound of formula (Ia):

wherein R¹ is as defined above;

c) ethynylating the compound of formula (Ia) to give a compound of formula (Va):

wherein R¹ is as defined above;

d) hydrolyzing the compound of formula (Va) to give gestodene, wherein the gestodene thus obtained has total impurities in an amount of no more than 0.5% by weight; and e) purifying gestodene as obtained in step d);

wherein the base used in step b) is selected from a metal carbonate; a metal bicarbonate; a metal hydroxide; a metal hydride; a metal acetate; ammonia; and an amine of formula $NR^5R^6R^7$ where $R^5$, $R^6$ and $R^7$ each independently represent H; a $(C_1-C_6)$alkyl optionally substituted by a hydroxyl; or a $(C_3-C_6)$cycloalkyl; and at least one of $R^5$, $R^6$ and $R^7$ is not H.

8. The process according to claim 7, wherein the base is selected from a metal carbonate, ammonia and an amine of formula $NR^5R^6R^7$.

9. The process according to claim 7, wherein the base is an amine of formula $NR^5R^6R^7$ in which $R^5$, $R^6$ and $R^7$ each independently represent H or a $(C_1-C_6)$alkyl optionally substituted by a hydroxyl; and at least one of $R^5$, $R^6$ and $R^7$ is not H.

10. The process according to claim 7, wherein the base is an amine of formula $NR^5R^6R^7$ in which $R^5$, $R^6$ and $R^7$ each independently represent H or a $(C_1-C_6)$alkyl;

and at least one of $R^5$, $R^6$ and $R^7$ is not H.

11. The process according to claim 7, wherein the base is an amine of formula $NR^5R^6R^7$ in which $R^5$ is H or a $(C_1-C_4)$alkyl and $R^6$ and $R^7$ each independently represent a $(C_1-C_4)$alkyl.

12. The process according to claim 7, wherein steps a) and b) are carried out as a one pot reaction.

13. The process according to claim 7, wherein steps c) and d) are carried out as a one pot reaction.

* * * * *